(12) United States Patent
Brown

(10) Patent No.: US 9,983,052 B1
(45) Date of Patent: May 29, 2018

(54) REDUCTION OF NOISE USING COHERENT LIGHT-SOURCE SQUEEZING

(71) Applicant: Robert G. Brown, Tustin, CA (US)

(72) Inventor: Robert G. Brown, Tustin, CA (US)

(73) Assignee: ROCKWELL COLLINS, INC., Cedar Rapids, IA (US)

( * ) Notice: Subject to any disclaimer, the term of this patent is extended or adjusted under 35 U.S.C. 154(b) by 745 days.

(21) Appl. No.: 14/278,494

(22) Filed: May 15, 2014

(51) Int. Cl.
 G01J 1/44 (2006.01)
 G01J 1/04 (2006.01)

(52) U.S. Cl.
 CPC .............. *G01J 1/44* (2013.01); *G01J 1/0422* (2013.01)

(58) Field of Classification Search
 CPC ..... G01B 9/02; G06F 1/39; G02F 1/01; G01J 4/00; G01J 1/044
 USPC ........ 250/208.1; 356/369, 486; 359/326–330
 See application file for complete search history.

(56) References Cited

U.S. PATENT DOCUMENTS

| 6,445,491 B2* | 9/2002 | Sucha | .......................... 359/326 |
| 2004/0018021 A1* | 1/2004 | Zhang | .................... H04L 9/0858 398/185 |
| 2005/0237533 A1* | 10/2005 | Lal | ........................... G01H 9/00 356/486 |

OTHER PUBLICATIONS

Bachor et al., A Guide to Experiments in Quantum Optics, Wiley-VCH (1998) pp. 278, 305 and 312.
Brown et al, 'Sub-Poissonian Photoelectron Statistics Produced Using Parametric Down Conversion with Feedback', Europhys. Lett., vol. 2, p. 279 (1986).
Li et al., 'Squeezing in travelling wave second harmonic generation', Optics Letters, vol. 18, p. 1961 (1993), 3 pages.
Saleh et al., Fundamentals of Photonics, Wiley-Interscience (2007), p. 885, 68 pages provided.
Schneider et al, 'Generation of strongly squeezed continuous-wave light at 1064nm', Optics Express, col. 2, p. 59 (1998).
Walls et al., Quantum Optics, Springer-Verlag (1994), p. 158, 172; 424 pages.
Wu et al, 'Generation of Squeezed States by Parametric Down Conversion', Phys. Rev. Letts., vol. 57, p. 2520, (1986).

* cited by examiner

*Primary Examiner* — Kevin Pyo
*Assistant Examiner* — Don Williams
(74) *Attorney, Agent, or Firm* — Donna P. Suchy; Daniel M. Barbieri

(57) ABSTRACT

An optical imaging system includes a coherent light generator, imaging optics and a detection system. The coherent light generator is configured to generate squeezed light. The imaging optics is arranged to direct the squeezed light from the coherent light generator onto a target object and to receive squeezed light reflected by the target object. The detection system includes a local oscillator configured to generate un-squeezed light at a same frequency and phase as the squeezed light, a combiner arranged to combine the received squeezed light from the imaging optics and the un-squeezed light from the local oscillator to provide combined light, and a detector arranged to receive and detect the combined light.

18 Claims, 8 Drawing Sheets

REDUCTION OF NOISE USING COHERENT LIGHT-SOURCE SQUEEZING

FIELD OF INVENTION

The present invention relates to the use of optical squeezing of light from a coherent light source and phase control of an imaging system for the reduction of shot noise in an optical imaging system.

BACKGROUND

Optical systems using optical squeezing of light are known. Such systems have been used to provide highly accurate measurement of infinitesimally small distance changes that might be caused by gravitational waves in interferometers [D. F Walls and G. J. Milburn, Quantum Optics, Springer-Verlag (1994), p. 158]. Optical squeezing of light has also been used in lab experiments for highly accurate measurement of phase change [D. F Walls and G. J. Milburn, Quantum Optics, Springer-Verlag (1994), p. 172], and has been proposed and demonstrated for gaining advantage in optical communications systems and cryptography systems, and absorption sensors [H. A. Bachor, A Guide to Experiments in Quantum Optics, Wiley-VCH (1998) pp. 305 and 312].

SUMMARY

According to one embodiment, an optical imaging system is provided comprising: a coherent light generator configured to generate squeezed light; imaging optics arranged to direct the squeezed light from the coherent light generator onto a target object and to receive squeezed light reflected by the target object; and a detection system comprising: a local oscillator configured to generate un-squeezed light at a same frequency and phase as the squeezed light; a combiner arranged to combine the received squeezed light from the imaging optics and the un-squeezed light from the local oscillator to provide combined light; and a detector arranged to receive and detect the combined light.

According to one aspect of the embodiment, the squeezed light is squeezed in at least one of phase or amplitude.

According to another aspect of the embodiment, the coherent light generator comprises: a laser emitting light at an angular frequency $\omega$; and a first non-linear optics element arranged to receive the light from the laser, and to generate light at the angular frequencies of $\omega$ and $2\omega$.

According to another aspect of the embodiment, the coherent light generator further comprises: a second non-linear optics element arranged to receive the light generated at the angular frequency of $2\omega$ from the first non-linear optics element, and to generate squeezed light at the angular frequency $\omega$.

According to another aspect of the embodiment, the second non-linear optics element comprises at least one of an optical parametric oscillator and an optical parametric amplifier.

According to another aspect of the embodiment, the optical imaging system of claim 1, further comprises: a first beam splitter arranged to receive the light generated at the angular frequencies of $\omega$ and $2\omega$ from the first non-linear optics element, to direct light at the angular frequency of $\omega$ to the local oscillator, and to direct light at the angular frequency of $2\omega$ to the second non-linear optics element.

According to another aspect of the embodiment, a detection scheme of the detection system is one of a homodyne scheme with no frequency offset between the received squeezed light from the imaging optics and the un-squeezed light from the local oscillator at the combiner, or a heterodyne scheme with a frequency offset between the received squeezed light from the imaging optics and the un-squeezed light from the local oscillator at the combiner.

According to another aspect of the embodiment, the local oscillator is configured to adjust a phase of the unsqueezed light.

According to another aspect of the embodiment, the local oscillator comprises at least one of a moving mirror, individually controllable mirrors in an array, an electro-optic element, an acousto-optic element, a frequency shifting element, or a rotating diffraction grating.

According to another aspect of the embodiment, the local oscillator is configured to adjust a phase of the unsqueezed light in a range of 0° to 180°.

According to another aspect of the embodiment, the detector comprises one or more photo-electric detectors.

According to another aspect of the embodiment, the detector comprises two detectors, and a signal combining element configured to add or subtract signals from the two detectors.

According to another aspect of the embodiment, the detector comprises a single element pixel.

According to another aspect of the embodiment, the detector comprises an array of multi-element pixels.

According to another aspect of the embodiment, the optical imaging system of claim 1, further comprises: processing electronics arranged to receive electrical signals from the detector.

According to another aspect of the embodiment, the processing electronics are configured to integrate the electrical signals form the detector to generate shot noise reduction.

According to another aspect of the embodiment, the shot-noise reduction improves image contrast, resolution, spatial frequency and super-resolution performance estimates.

According to another aspect of the embodiment, the processing electronics are configured to produce images that are 2-dimensional, 3-dimensional, or 4-dimensional.

According to another aspect of the embodiment, the optical imaging system is one of a LIDAR, LADAR, camera, microscope, telescope, or hyper-spectral imaging system.

DETAILED DESCRIPTION

Optical Squeezing and Shot Noise

Basic principles of optical squeezing are provided below.

A laser beam may be seen as a coherent beam of light moving in a straight line direction. This is a classical optics concept with waves of light all oscillating in step as they propagate.

The quantum mechanical equivalent of such a classical monochromatic electromagnetic wave is called a coherent state. The states may be represented in Dirac notation as $|\alpha\rangle$.

Figure 1:
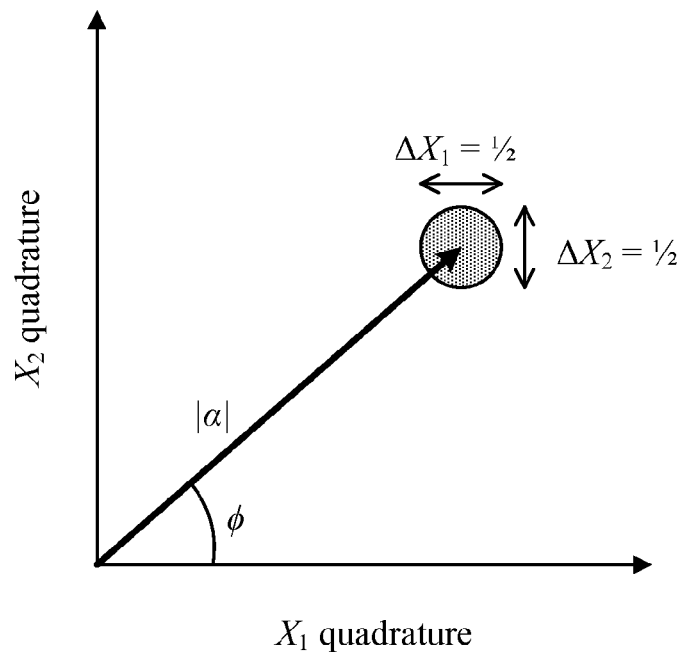
FIG. 1 is a phasor diagram illustrating a coherent light state and quantum uncertainty along dimensionless quadratures.

For a linearly polarized mode of angular frequency $\omega$ enclosed in a cavity of volume V, $\alpha$ may be defined as: $\alpha = X_1 + i X_2$, where $X_1$ and $X_2$ are defined as dimensionless quadratures of the field within the laser cavity. $\alpha$ can be separated into its amplitude, $|\alpha|$, and phase, $\varphi$, by writing: $\alpha = |\alpha| e^{i\varphi}$ with $|\alpha| = (X_1^2 + X_2^2)^{1/2}$, $X_1 = |\alpha| \cos \varphi$, and $X_2 = |\alpha| \sin \varphi$. Thus, $|\alpha\rangle$ can be represented as a phasor of length $|\alpha|$ with phase angle $\varphi$ as shown in FIG. 1. The phasor diagram of FIG. 1 illustrates the coherent state $|\alpha\rangle$, where the quantum uncertainty is shown by a circle of diameter ½ at the end of the phasor.

The coherent state may related to the classical electrical field amplitude $\epsilon_0$ through the equation: $|\alpha| = (\in_0 V / 4 \hbar \omega)^{1/2} \cdot \epsilon_0$, where $\in_0$ is the electrical permittivity, V is the laser cavity volume, $\omega$ is the mode angular frequency, and $\hbar$ is planck's constant.

The classical electromagnetic energy due to the mode in the laser cavity may be calculated to be: $E_{classical} = V \in_0 \epsilon_0^2 / 4$, which is then $E_{classical} = \hbar \omega |\alpha|^2$. This links to the quantum theory of the electromagnetic harmonic oscillator through the standard equation: $E_{quantum} = \langle n \rangle \hbar \omega + ½ \hbar \omega$, where $\langle n \rangle$ is the average number of photons excited in the cavity at angular frequency $\omega$. Only the first term equates to the classical energy due to $\epsilon_0$, so, by setting $E_{classical} = \langle n \rangle \hbar \omega$, it becomes clear that $|\alpha| = (\langle n \rangle)^{1/2}$. The length of the vector that represents the coherent state $|\alpha\rangle$ in a phasor is equal to $(\langle n \rangle)^{1/2}$.

Both the length and angle of the coherent state are uncertain, as seen in FIG. 1, which is in contrast to the classical situation. The quantum uncertainty of a coherent state can also be seen in FIG. 2, which illustrates an uncertainty circle of a coherent state introducing both photon number n and phase $\varphi$. The phase uncertainty is only well defined when $|\alpha| = (\langle n \rangle)^{1/2} \gg 1$.

Both the photon number uncertainty and the uncertainty in the optical phase can be calculated. From FIG. 2, the photon number uncertainty $\Delta n$ is $(|\alpha| + ¼)^2 - (|\alpha| - ¼)^2 = |\alpha| = (\langle n \rangle)^{1/2}$. Thus, the coherent states have Poisson statistics, which causes shot noise in optical detection. Shot noise arises from the quantum uncertainty in the light. Uncertainty in the optical phase can also be calculated, and is given by $\Delta \varphi = (½)/(\langle n \rangle)^{1/2}$. The number phase uncertainty is thus $\Delta n \Delta \varphi \geq ½$, in accordance with Heisenberg uncertainty principle. That is the photon number and phase of an optical wave cannot be known with perfect precision at the same time.

Figure 2:
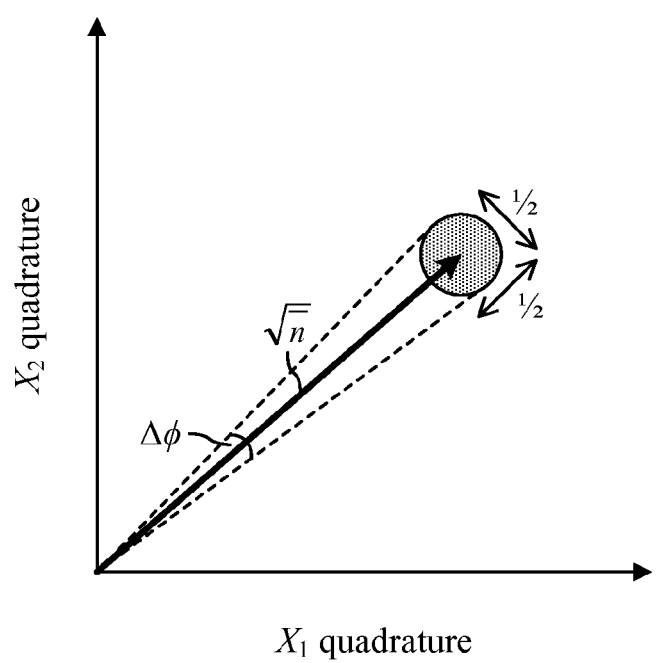
FIG. 2 is a phasor diagram illustrating a coherent light state and quantum uncertainty for amplitude and phase.
Figure 3A:
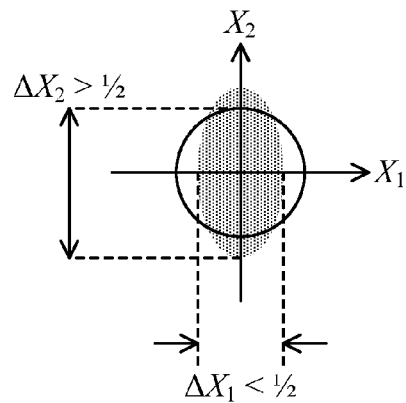
FIG. 3A is a diagram illustrating a squeezed vacuum.
Figure 3B:
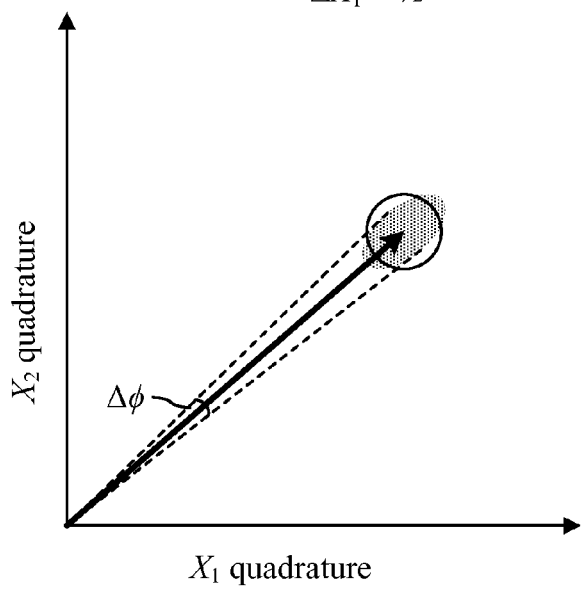
FIG. 3B is a phasor diagram illustrating phase squeezed light.
Figure 3C:
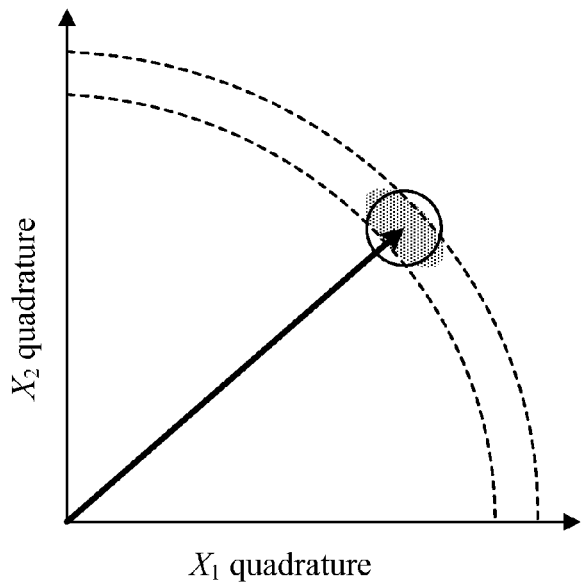
FIG. 3C is a phasor diagram illustrating amplitude squeezed light.

Optical squeezing can be understood with respect to squeezing the circle in FIG. 2, as illustrated in FIG. 3A-FIG. 3B, which illustrate quadrature squeezed states. FIG. 3A illustrates a squeezed vacuum. FIG. 3B illustrates phase squeezed light. FIG. 3C illustrates amplitude squeezed light. The knowledge/precision of one variable can be traded for lack of the knowledge/precision in the other variable, where in this case the variables are the optical phase and photon number.

An important type of squeezed states are photon number (n) squeezed states. One can have perfectly defined number states with no knowledge of phase, and vice versa. In coherent states with larger photon number fluctuations ($\Delta n = (\langle n \rangle)^{1/2}$) there is a better defined phase.

Homodyne Detection of Squeezed-Light and Reducing Shot Noise

Figure 4:
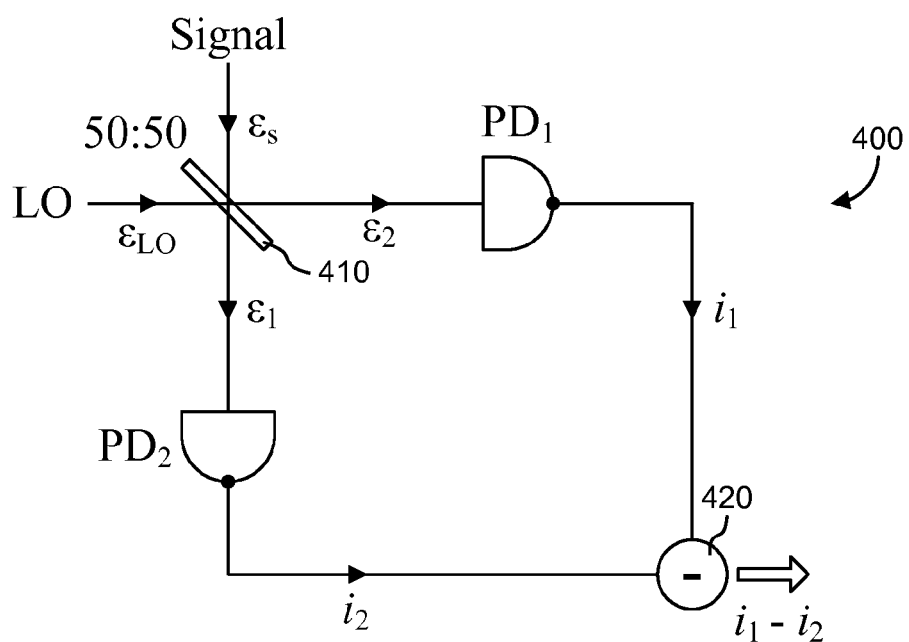
FIG. 4 is a schematic illustrating a balanced homodyne detector.

FIG. 4 is a schematic illustrating a balanced homodyne detector 400 for detecting squeezed light, where the system employs an interferometric detection scheme. While FIG. 4 illustrates homodyne detector for detecting squeezed light according to a homodyne scheme with no frequency offset between reference light (from local oscillator (LO) in FIG. 4) and squeezed light (Signal in FIG. 4), alternatively, detection may be performed according to a heterodyne scheme with a frequency offset between the reference beam and the squeezed light. The detector in FIG. 4 employs a balanced detection, using two photodetectors ($PD_1$ and $PD_2$) simultaneously, to eliminate random classical thermal noise almost completely.

The detector 400 in FIG. 4 includes a combiner 410, which may be a polarizing beam splitter, to combine the squeezed light (the Signal) with reference light from the local oscillator (LO). The local oscillator (LO) is configured to adjust the phase of the reference light to be in phase with the squeezed light. The combiner 410 provides combined light of one polarization to a first photodetector $PD_1$, and combined light of another polarization to a second photodetector $PD_2$. The detector 400 further includes a signal combining element 420 configured to subtract ($i_1 - i_2$) or add ($i_1 + i_2$) the signals from the second photodetector $PD_2$ ($i_2$) and the first photodetector $PD_1$ ($i_1$).

In the homodyning detection scheme in the detector 400 of FIG. 4 the reference-beam from the LO is combined together with the signal beam. In the homodyning, the wavefront of the reference light may aligned with that of the squeezed light to maximize homodyning efficiency. This may be achieved, for example, by adjusting the phase of the reference light to be in phase with the squeezed light by adjusting the local oscillator (LO).

While FIG. 4 illustrates a detection scheme with balanced detection, the invention is not so restricted. For example, in a sufficiently cooled or low noise design photodetector, balanced detection may not be required, and one of the detectors may be eliminated. Detection schemes with a single detector may have advantages in certain optical applications, such as in LIDAR (Light Detection and Ranging) designs, to reduce overhead cost, complexity and size.

The output of the interferometric style of detection according to the detector of FIG. 4 is phase sensitive. By changing the signal combining element 420 from subtracting, $i_1-i_2$, to adding, $i_1+i_2$, the amplitude squeezed light may be detected along with its sub-Poissonian photon statistical properties.

Using squeezed light as the illumination in the optical system, the noise may be reduced below the shot noise limit in a balanced, or in a thermal noise free detector arrangement.

Generation of Squeezed Light

The squeezed light may be generated using an appropriate generation scheme, such as, for example, resonance fluorescence, parametric oscillator, and nonlinear optical 4 wave mixing configurations. For example, parametric oscillation [see L. A. Wu et al, '*Generation of Squeezed States by Parametric Down Conversion*', Phys. Rev. Letts., vol. 57, p. 2520, (1986)] and 4-wave mixing can both produce powerful squeezed laser beams. The principles and practice of parametric-oscillator/amplifier lasing have been described [see B. E. A. Saleh and M. C. Teich, Fundamentals of Photonics, Wiley-Interscience (2007), p. 885].

Figure 5A:
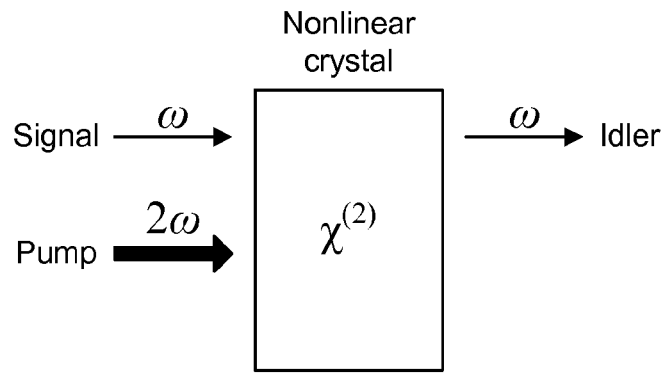
FIG. 5A is a schematic of an arrangement for a degenerate parametric amplifier.

FIG. 5A is a schematic of an arrangement for a degenerate parametric amplifier capable of creating powerful squeezed light laser beams. In particular, FIG. 5A illustrates a second order nonlinear optical (NLO) crystal pumped by a laser pump at an angular frequency $2\omega$, i.e., the angular frequency of the laser light is $2\omega$. The pumped crystal amplifies a signal at an angular frequency $\omega$, i.e. the angular frequency of the signal light is $\omega$.

Figure 5B:
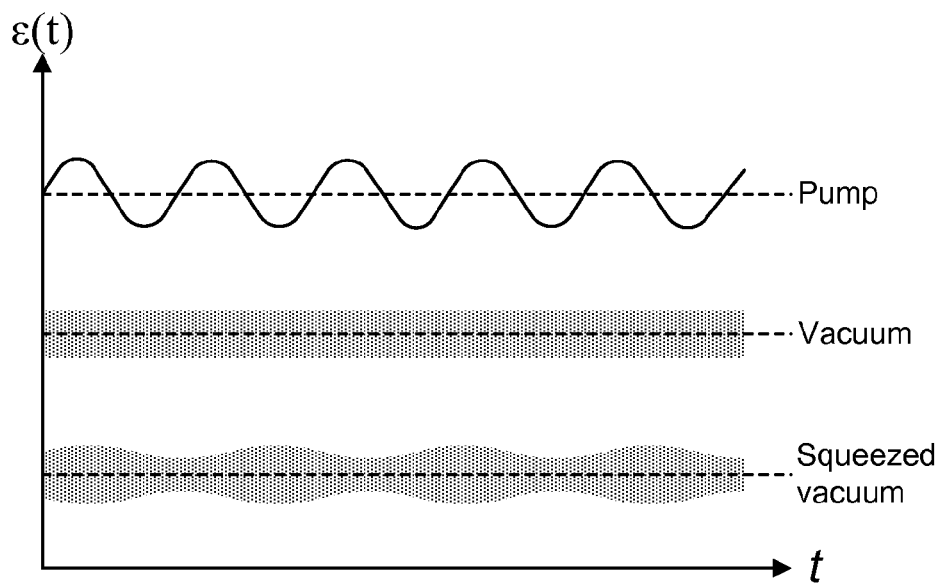
FIG. 5B is a graph illustrating the light intensity as a function of time for pump signal, vacuum and squeezed vacuum.

FIG. 5B illustrates the intensity of the output signal from the NLO crystal with no input signal at $\omega$, i.e. in the vacuum state, as compared to the pump intensity and the vacuum state intensity. With no signal, the NLO crystal deamplifies the vacuum modes, producing quadrature squeezed vacuum states.

Figure 6A:
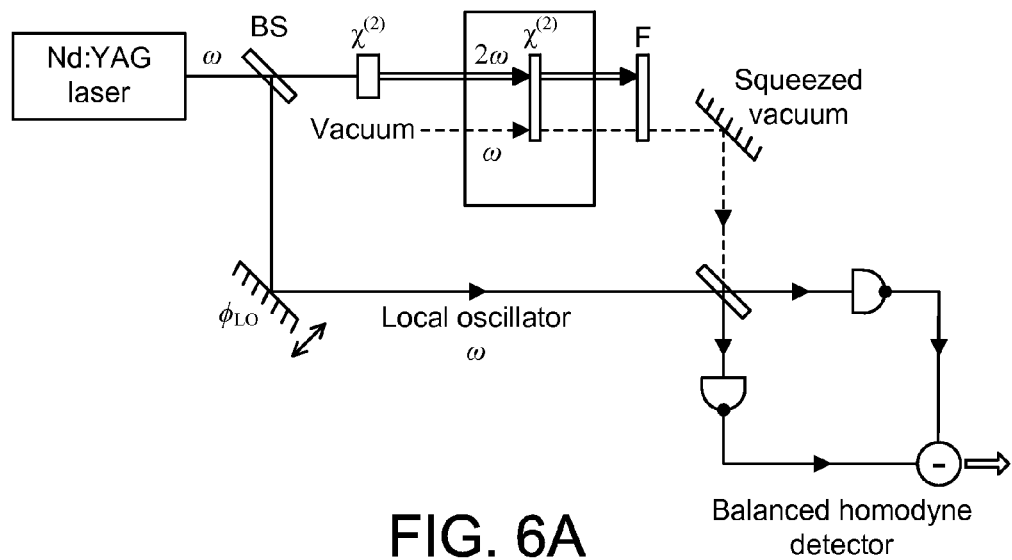
FIG. 6A is a schematic of an optical system combining features of the arrangements of the detector of FIG. 4 and the amplifier of FIG. 5A.
Figure 6B:
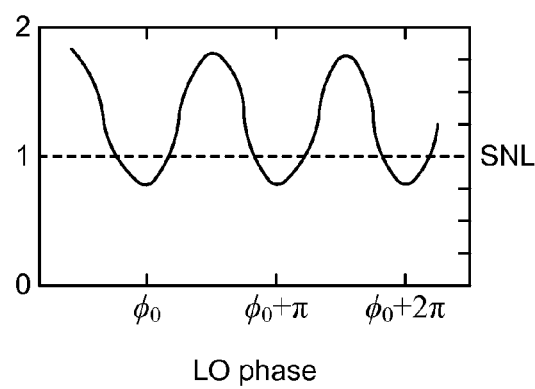
FIG. 6B is a graph illustrating the noise voltage as the signal to noise level (SNL) detected as a function of the LO phase.

FIG. 6A is a schematic of an optical system combining features of the arrangements of the detector of FIG. 4 and the degenerate parametric amplifier of FIG. 5A. FIG. 6B illustrates the noise voltage as the signal to noise level (SNL) detected as a function of the LO phase. It should be noted that variation of noise voltage varies with phase of the LO as the phase varies over 180° ($\pi$ radian) and dips below unity. This indicates that the squeezed noise level reduction dips below the shot noise level, SNL=1.

Losses in Squeezed Light Applications

Losses in squeezed light detection systems may be degraded by scattering and absorbing atmospherics and optical components in any overall complete system. The squeezed light must propagate through various optical components, in addition to the atmosphere, where scattering and absorption losses may occur. Mismatch of the LO reference light and the signal light in the homodyning process may degrade in detection efficiency. Each such loss, mismatch or inefficiency will reduce the degree of squeezing and thus reduce the low noise advantage. This is very different to normal optics, where losses may be compensated for by increasing beam power.

Quantification of the losses in a squeezed system may be predicted, where all passive losses are taken to behave as beamsplitters, excluding any nonlinear processes.

Loss transforms the squeezed ellipse desired (see FIGS. 3A-3C) towards a circle. The input squeezed state can generally be described in Dirac notation as $|\alpha, r, \varphi\rangle$, where $\alpha$ is the amplitude, r the position, and $\varphi$ the phase, and the output state after the beam-splitter, can be described as $|\alpha', r', \varphi'\rangle$. Intensity is reduced such that $|\alpha|^2=\rho|\alpha|^{2'}$ where $\eta$ is the loss (efficiency) of the process. Based on this analysis it can be found that noise suppression is reduced linearly with loss $\eta$, in analogy to the case of sub-Poissonian light [see R. G. W. Brown et al, 'Sub-Poissonian Photoelectron Statistics Produced Using Parametric Down-Conversion with Feedback', Europhys. Lett., vol. 2, p. 279 (1986).]. Strong squeezing is easily lost in a system with limited efficiency.

Figure 7:
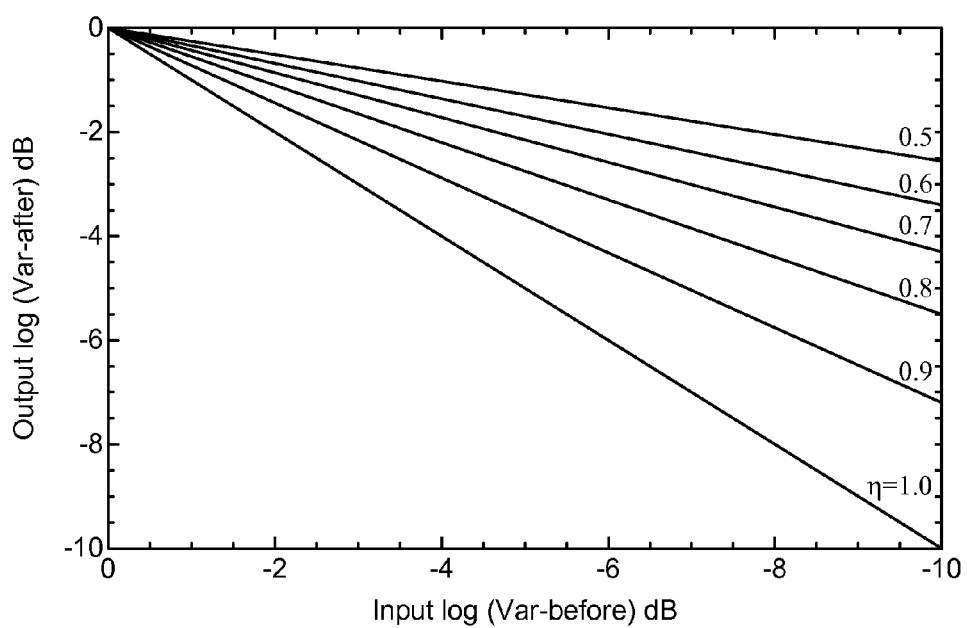
FIG. 7 is a graph illustrating the variance of light after reaching the beam splitter as a function of the variance of light before reaching the beam splitter for different loss values.

FIG. 7 illustrates the quantitative effects of different efficiencies on the minimum variance of the squeezed state. In particular, FIG. 7 illustrates the quantitative effects of different losses $\eta$ on the minimum variance of the squeezed state in dB. In FIG. 7, variance after the beam splitter is plotted against variance (Var) before the beam splitter. The loss is given by the relation (1−Var-after)=$\eta$(1−Var-before). Thus, a loss $\eta$ of 0.5 transforms −3 dB squeezing into −1.3 dB. For −10 dB squeezing, the result is −2 dB due to $\eta$. Thus, losses have a strong effect and should be avoided.

Optical Imaging System

Figure 8:
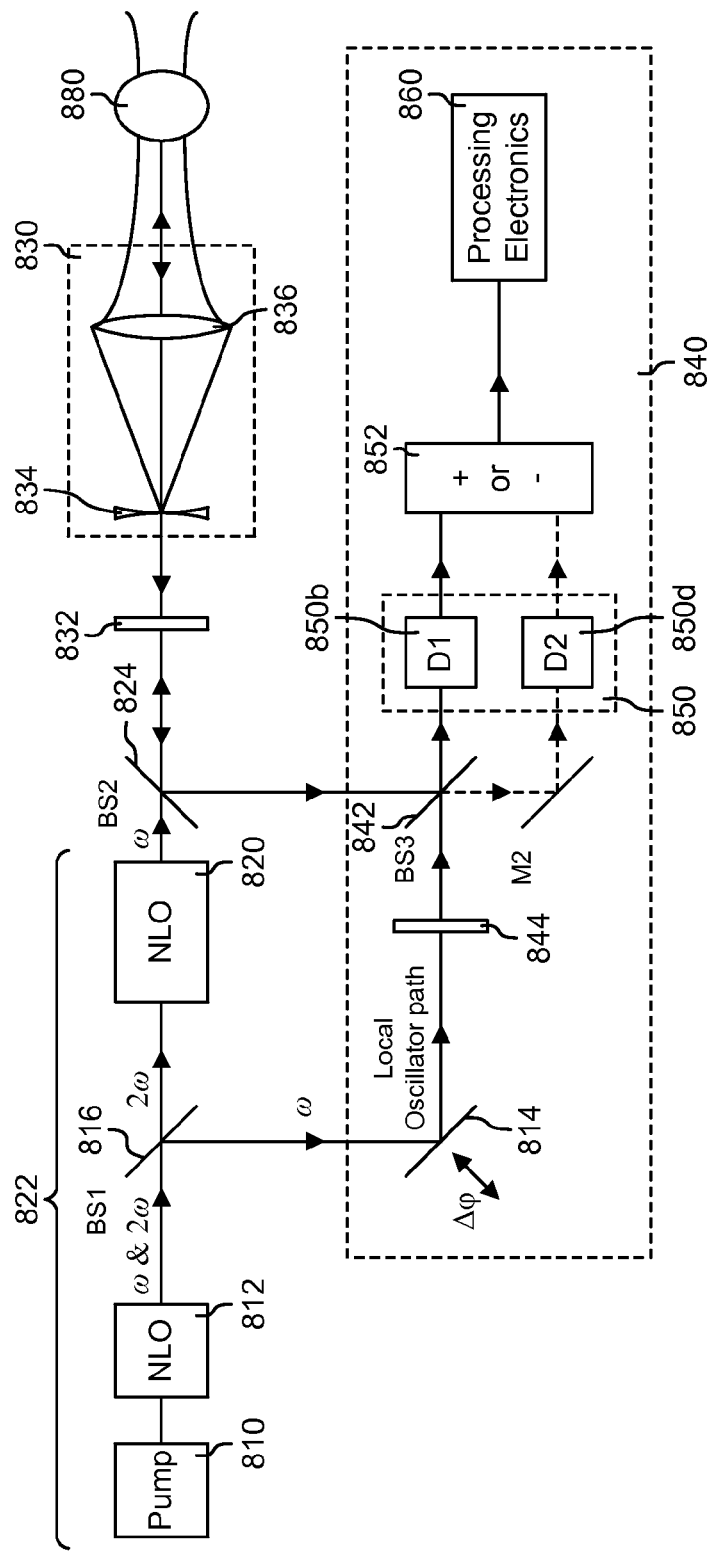
FIG. 8 is a schematic illustrating a squeezed light imaging system according to an embodiment of the invention.

FIG. 8 illustrates a squeezed light imaging system 800 according to an embodiment of the invention.

The imaging system 800 includes a pump laser 810 emitting light at an angular frequency $\omega$ and a first non-linear optics element (NLO) 812 arranged to receive the light from the laser, and to generate light at the angular frequencies of $\omega$ and $2\omega$. For example, the pump laser 810 may be a Nd:YAG laser emitting light at a wavelength 1.064 microns ($\omega$), which light is frequency doubled to have a wavelength of 532 nm ($2\omega$) by disposing the NLO 812, such as for example a crystal of $Ba_2NaNb_5O_{15}$, inside a laser cavity of the laser pump 810. For such a Nd:YAG laser and crystal of $Ba_2NaNb_5O_{15}$, the frequency conversion is very efficient, typically ≥98% conversion efficiency, such that there is only a very weak output at 1.064 microns ($\omega$). This weak output at $\omega$ is appropriate for the light of the LO 814 which is used to generate un-squeezed light at $\omega$, to be combined with reflected light from the target object 880. The pump laser 810 may alternatively be a semiconductor laser diode providing laser light at the frequency $\omega$.

The optical system 800 has a first beam splitter 816. The first beam splitter 816 is arranged to receive the light generated at the angular frequencies of $\omega$ and $2\omega$ from the first non-linear optics element 812, and to direct light at the angular frequency of $\omega$ to the LO 814. The first beam splitter 816 may be a dichroic beam splitter, configured to separate the two laser frequencies $\omega$ and $2\omega$. The first beam splitter 816 further directs light at the angular frequency of $2\omega$ to a second non-linear optics element 820. Preferably, the light at the frequency at $2\omega$ from the first beam splitter 816 directed to the second non-linear optics element 820 is much more powerful than the light at the frequency at $\omega$ from the first beam splitter 816 directed to the LO 814.

The light at the frequency at $2\omega$ from the first beam splitter 816 directed into the second non-linear optics element 820 undergoes a process of parametric down-conversion, in which photons with frequency $2\omega$ are converted into correlated pairs of photons of frequency $\omega$. It is this sub harmonic field at $\omega$ that is produced in the squeezed state. The second non-linear optics element 820 may be, for example, a crystal of $MgO:LiNbO_3$ which provides the parametric down conversion of 532 nm green light ($2\omega$) to 1.063 nm light ($\omega$), at a conversion efficiency of around 98%.

The combination of the pump laser 810, first non-linear optics element 812 and second non-linear optics element 820 together comprise portions of a coherent light generator 822 configured to generate light at the angular frequency $\omega$. Thus, the coherent light generator 822 provides a powerful beam of squeezed laser light at a frequency $\omega$, which is the same as the un-squeezed LO laser frequency from the LO 814. Generating strongly squeezed (7.2 dB of squeezing)

continuous wave light at 1.064 micron is described, for example, in [K. Schneider et al, 'Generation of strongly squeezed continuous-wave light at 1064 nm', Optics Express, col. 2, p. 59 (1998)].

The optical system 800 further includes a second beam splitter 824. The second beam splitter 824 may be a polarizing beam splitter, such as a Wollaston prism. The second beam splitter 824 may have an antireflection coating for light at the frequency $\omega$, to minimize any surface losses. The second beam splitter 824 receives the light at the frequency $\omega$ from the second non-linear optics element 820, and directs that light toward imaging optics 830. The imaging optics 830 is arranged to direct the squeezed light at $\omega$ from the coherent light generator 822 onto a target object 880 and to receive squeezed light reflected by the target object 880.

The second beam splitter 824 is not limited to transmitting a particular polarization of light. For the sake of illustration, it is assumed that the second beam splitter 824 is a polarizing beam splitter transmitting vertical polarization and that the squeezed light from the coherent light generator 822 provides entirely vertically polarized light at the frequency $\omega$. Alternatively, for example, the second beam splitter 824 could be a polarizing beam splitter transmitting horizontal polarization and where the coherent light generator 822 provides entirely horizontally polarized squeezed light at the frequency $\omega$.

The optical system 800 may include a quarter wave plate 832. The vertically polarized squeezed light is transmitted by the second beam splitter 824 to a quarter wave plate 832, appropriately oriented to output circularly polarized light. The reason for this is that when the light is eventually reflected off the target object 880, the circular polarization is reversed in handed-ness, and so when the reflected light later travels back though the quarter wave plate 832, the signal from the target object 880 will exit from the quarter wave plate 832 with an orthogonal polarization, or a horizontally polarization in this case. Therefor the reflected light from the target object 880 will be directed by the second beam splitter 824 down into a detection system 840 of the system 800, where the reflected light is combined with unsqueezed light and detected by a detector as discussed further below.

The circularly polarized squeezed laser light at frequency $\omega$ is directed from the quarter wave plate 832 and imaged onto the target object 880 via imaging optics 830. The imaging optics 830 may take the form of a number of different arrangements according to the application. For example, the imaging optics 830 may be a single lens, a beam expanding and focusing lens pair, such as the beam expanding lens 834 and focusing lens 836 illustrated in FIG. 8. In a LIDAR optical system, the imaging optics 830 may include a Cassegrain telescope and a post telescope scanning mirror-pair to sweep the laser beam around the sky and permit volume and 3-dimensional images to be acquired.

As discussed above, light that hits the target object 880 to be imaged is reflected in a reversed circular polarization condition, i.e., right handed polarization will be converted to left handed polarization, for example. Some or most of that reflected light will be collected by the imaging optics 830, pass through the quarter wave plate 832 which converts the reversed circular polarized light into horizontally polarized light, i.e., orthogonally to the incident vertically polarized light from the second beam splitter 824. That horizontally polarized light, upon entering the second beam splitter 824 is now directed down to the optical chain of the detection system 840, and cannot reenter the second non-linear optics element 820 where it was originally generated. This target object 880 light enters a combiner 842, which may be a beam splitter, of the detection system 840, where it meets and combines with the unsqueezed light from the LO 814 of the detection system 840.

For the case where the unsqueezed light from the second nonlinear optical element 820 provides vertically polarized light based on vertically polarized light from the laser 810 transmitted through the first beam splitter 816, the laser 810 and first nonlinear optical element 812 provides vertically polarized light at both frequencies $\omega$ and $2\omega$.

As discussed with respect to FIG. 6B, the reduction in shot noise is achieved by adjusting the phase of the reference light from the LO 814, which combines with the squeezed light, to an appropriate value. In this regard, the LO 814 may comprise a mirror, which can be a piezo-driven mirror, or any other phase changing device. Changing the physical position of the mirror surface by up to $\pi$-radians, i.e., $\leq 180°$ ($\pi$ radians, or up to a half wavelength) allows for the achievement of a minimum shot noise level in this imaging system. For area imaging applications, the LO 814 may include a MEMS array of mirrors allowing for independent phase control for individual image pixels.

The phase adjusted LO light from the LO 814 is directed through a half wave plate 844, appropriately oriented to turn the incoming vertically polarized light into horizontally polarized light, which is the same type of polarization as that of the reflected light from the target object 880 that is directed by the second beam splitter to the combiner 842. Thus, squeezed light reflected from the target object 880 that is incident on the combiner 842 has the same polarization as the unsqueezed light incident on the combiner from the LO 814.

Figure 9:
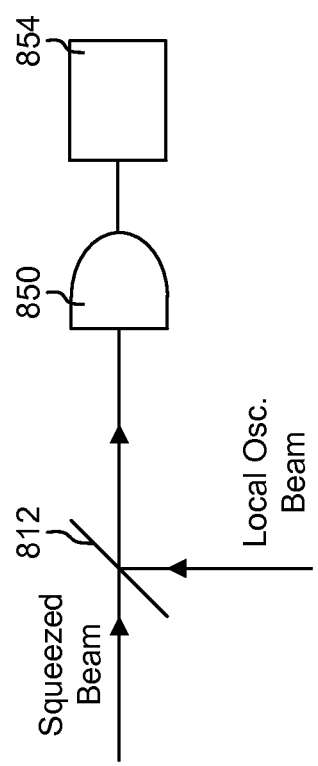
FIG. 9 is a schematic illustrating an example of a homodyne scheme for combining a squeezed light beam and a LO reference beam.

FIG. 9 illustrates an example of a homodyne scheme for combining a squeezed light beam and a LO reference beam. The combiner 842 combines the squeezed beam from the target object 880 (see FIG. 8) with the LO reference beam and directs the two together to the detector 850 which provides an appropriate signal to the spectrum analyzer 854. A key condition at the combiner 842 is that the wavefronts of the two incoming beams overlap as exactly as possible to maximize the homodyning efficiency upon photo detection Returning to FIG. 8, the detection system 840 includes a detector 850, which may comprise a single detector, or multiple detectors, such as the first detector 850a and second detector 850b. The detector is arranged to receive and detect the combined light from the combiner 842.

The detector 850 may vary according to the application. If the detector is sufficiently thermal noise free, such as for a cooled or very low noise avalanche photodiode in Geiger or sub-Geiger (linear) mode, then only a single detector 850 may be needed in which to homodyne detect the incoming two overlapping beams, i.e., squeezed signal and reference LO. If the detectors have some random, uncorrelated thermal noise level, this can mostly be eliminated by detecting in two channels, using the first detector 850a and second detector 850b and then adding/subtracting according to whether phase or amplitude shot noise is desired to be reduced. When thermal noise is eliminated, shot noise is usually the next most dominant noise source. In this case, the shot noise as well as thermal noise may be eliminated.

Imaging in the Squeezed Light System

Imaging in the squeezed light system includes at least two options.

In a first option, the laser beam illuminating the target object 880 is quite small in diameter and each of the first detector 850a and second detector 850b is a single pixel detector. As the laser beam is scanned across the target object 880, the first detector 850a and second detector 850b will output a shot noise reduced electrical signal that can be constructed into an image of the object in the standard way.

However, if the laser beam illuminating the target object 880 is somewhat larger, the first detector 850*a* (and second detector 850*b* if necessary) can be replaced by detector arrays, such as CMOS-imagers, such as those found in electronic cameras. When the second detector 850*b* is employed as well as the first detector 850*a*, corresponding pixels in the two arrays can be added or subtracted to achieve the desired type of phase or amplitude squeezing. In this case, the optical system 800 includes a signal combining element 852 configured to add or subtract signals from the first detector 850*a* and the second detector 850*b*.

The system 800 may further include processing electronics 860 arranged to receive electrical signals from the detector 850. Signal to noise ratio improves as the square root of the number of images integrated. In this case, the processing electronics 860 are configured to integrate the electrical signals form the detector 850 to generate shot noise reduction. Further, integration improves contrast and resolution within the image.

As seen with respect to the discussion with respect to FIG. 7, for a system of 50% optical efficiency, 2 to 3 dB of noise reduction may be obtained through application of sufficiently squeezed light. Achieving 3 dB in noise (~half-power) performance normally requires 4 integrations. The benefit of squeezing is that similar quality improvements in a 1 frame image, in a ¼ the time of the standard integration processing procedure is achievable.

Reducing the system losses so that the loss $1{-}1=0.75$ provides 4.5 to 5 dB noise (~one third power) improvement possibility. This improvement corresponds to ~9 integrations to achieve improved contrast/resolution images in one 'shot', i.e., a single frame. The benefit of squeezing now is that similar quality improvements may be obtained in a 1 frame image, in ⅑ the time of the standard integration processing procedure. By further integrating for the original time using a shot noise reduced imager, a further factor of 3 to 9 in noise reduction may be obtained.

Application of Optical Squeezing to LIDAR

The discussion above assumes a continuous wave laser source, but optical light squeezing detection may include a pulsed laser source. For example, LIDAR imaging, which used 2-dimensional or 3-dimensional imaging generally, requires a pulsed laser source, for range discrimination. As discussed above, in a LIDAR optical system, the imaging optics 830 may include a Cassegrain telescope and a post telescope scanning mirror-pair to sweep the laser beam around the sky and permit volume and 3-dimensional images to be acquired.

Further in the case of LIDAR imaging, the laser 810 may be a pulsed laser. Pulsed laser squeezing is known and described for example in [H. A. Bachor, A Guide to Experiments in Quantum Optics, Wiley-VCH (1998), p. 278]. Indeed, pulsed laser squeezing may provide squeezing results with very high intensities and nonlinearities that can be achieved with laser pulses.

The high peak intensities of short laser pulses allow realization of direct single pass travelling wave second harmonic generation, $\omega$ to $2\omega$ conversion, as provided in the optical system illustrated in FIG. 8. If $\Gamma$ is the single pass second harmonic conversion efficiency, the noise suppression is $1-\Gamma$ [R. D. Li et al., 'Squeezing in travelling wave second harmonic generation', Optics Letters, vol. 18, p. 1961 (1993)]. This effect provides the possibility of good squeezing with low shot noise provided where most of the laser light is converted to the second harmonic. For a LIDAR application, the laser 810 may be a Nd:YAG laser, for example, which is appropriate as a LIDAR laser source, and can be easily pulsed and frequency doubled.

In the case of a LIDAR, or LADAR (Laser Detection and Ranging) application it may be desirable to use heterodyne detection using a frequency offset LO, instead of homodyne detection with no frequency offset LO, to remove directional ambiguity of object target 880 motion.

The embodiments of the invention have been described in detail with particular reference to preferred embodiments thereof, but it will be understood by those skilled in the art that variations and modifications can be effected within the spirit and scope of the invention.

What is claimed is:

1. An optical imaging system comprising:
   a coherent light generator configured to generate squeezed light;
   imaging optics arranged to direct the squeezed light from the coherent light generator onto a target object and to receive squeezed light reflected by the target object; and
   a detection system comprising:
      a local oscillator configured to generate un-squeezed light at a same frequency and phase as the squeezed light;
      a combiner arranged to combine the received squeezed light from the imaging optics and the un-squeezed light from the local oscillator to provide combined light; and
      a detector arranged to receive and detect the combined light,
   wherein the coherent light generator comprises:
      a laser emitting light at an angular frequency $\omega$; and
      a first non-linear optics element arranged to receive the light from the laser, and to generate light at the angular frequencies of $\omega$ and $2\omega$.

2. The optical imaging system of claim 1, wherein the squeezed light is squeezed in at least one of phase or amplitude.

3. The optical imaging system of claim 1, wherein the coherent light generator further comprises:
   a second non-linear optics element arranged to receive the light generated at the angular frequency of $2\omega$ from the first non-linear optics element, and to generate squeezed light at the angular frequency $\omega$.

4. The optical imaging system of claim 3, further comprising:
   a first beam splitter arranged to receive the light generated at the angular frequencies of $\omega$ and $2\omega$ from the first non-linear optics element, to direct light at the angular frequency of $\omega$ to the local oscillator, and to direct light at the angular frequency of $2\omega$ to the second non-linear optics element.

5. The optical imaging system of claim 1, wherein the second non-linear optics element comprises at least one of an optical parametric oscillator and an optical parametric amplifier.

6. The optical imaging system of claim 1, wherein a detection scheme of the detection system is one of a homodyne scheme with no frequency offset between the received squeezed light from the imaging optics and the un-squeezed light from the local oscillator at the combiner, or a heterodyne scheme with a frequency offset between the received squeezed light from the imaging optics and the un-squeezed light from the local oscillator at the combiner.

7. The optical imaging system of claim 1, wherein the local oscillator is configured to adjust a phase of the unsqueezed light.

8. The optical imaging system of claim 7, wherein the local oscillator comprises at least one of a moving mirror, individually controllable mirrors in an array, an electro-optic element, an acousto-optic element, a frequency shifting element, or a rotating diffraction grating.

9. The optical imaging system of claim 7, wherein the local oscillator is configured to adjust a phase of the unsqueezed light in a range of 0° to 180°.

10. The optical imaging system of claim 1, wherein the detector comprises one or more photo-electric detectors.

11. The optical imaging system of claim 1, wherein the detector comprises two detectors, and a signal combining element configured to add or subtract signals from the two detectors.

12. The optical imaging system of claim 1, wherein the detector comprises a single element pixel.

13. The optical imaging system of claim 1, wherein the detector comprises an array of multi-element pixels.

14. The optical imaging system of claim 1, further comprising:
processing electronics arranged to receive electrical signals from the detector.

15. The optical imaging system of claim 14, wherein the processing electronics are configured to integrate the electrical signals form the detector to generate shot noise reduction.

16. The optical imaging system of claim 15, wherein the shot-noise reduction improves image contrast, resolution, spatial frequency and super-resolution performance estimates.

17. The optical imaging system of claim 14, wherein the processing electronics are configured to produce images that are 2-dimensional, 3-dimensional, or 4-dimensional.

18. The optical imaging system of claim 15, wherein the optical imaging system is one of a LIDAR, LADAR, camera, microscope, telescope, or hyper-spectral imaging system.

* * * * *